US009554726B2

(12) United States Patent
Krummenacker et al.

(10) Patent No.: US 9,554,726 B2
(45) Date of Patent: Jan. 31, 2017

(54) HYPERPOLARIZATION APPARATUS AND METHOD FOR ADMINISTRATION OF A HYPERPOLARIZED LIQUID CONTRAST AGENT

(71) Applicant: Johann Wolfgang Goethe-Universität Frankfurt am Main, Frankfurt am Main (DE)

(72) Inventors: Jan Krummenacker, Beckingen (DE); Thomas Prisner, Bad Vilbel (DE); Vasyl Denysenkov, Frankfurt am Main (DE); Laura Schreiber, Mainz (DE); Kerstin Münnemann, Monzernheim (DE)

(73) Assignee: Johann Wolfgang Goethe-Universität Frankfurt am Main, Frankfurt am Main (DE)

( * ) Notice: Subject to any disclaimer, the term of this patent is extended or adjusted under 35 U.S.C. 154(b) by 361 days.

(21) Appl. No.: 13/721,173

(22) Filed: Dec. 20, 2012

(65) Prior Publication Data
US 2013/0184565 A1  Jul. 18, 2013

Related U.S. Application Data

(63) Continuation of application No. PCT/EP2011/003125, filed on Jun. 24, 2011.

(30) Foreign Application Priority Data

Jun. 24, 2010 (DE) ......................... 10 2010 017 568

(51) Int. Cl.
*A61B 5/05* (2006.01)
*A61B 5/055* (2006.01)
(Continued)

(52) U.S. Cl.
CPC ............. *A61B 5/055* (2013.01); *G01R 33/282* (2013.01); *G01R 33/62* (2013.01); *G01N 24/12* (2013.01); *G01R 33/5601* (2013.01)

(58) Field of Classification Search
None
See application file for complete search history.

(56) References Cited

U.S. PATENT DOCUMENTS

| | | | |
|---|---|---|---|
| 5,603,320 A | 2/1997 | Dumoulin et al. | ........... 600/423 |
| 6,108,574 A | 8/2000 | Ardenkjaer-Larsen | |

(Continued)

FOREIGN PATENT DOCUMENTS

| | | | | |
|---|---|---|---|---|
| EP | 1746431 A1 | 1/2007 | ............. | G01R 33/28 |
| EP | 22119457 A1 | 11/2009 | ............. | A61K 49/06 |

OTHER PUBLICATIONS

Vahala et al. ("A study of the use of Overhauser enhancement to assist with needle and catheter placement during interventional MRI"; Journal of Magnetic Resonance 157, 298-303; 2002).*

(Continued)

*Primary Examiner* — Amanda Lauritzen Moher
*Assistant Examiner* — Shahdeep Mohammed
(74) *Attorney, Agent, or Firm* — Sunstein Kann Murphy & Timbers LLP

(57) ABSTRACT

A hyperpolarized liquid contrast agent is for use in a MRT device. The liquid contrast agent passes through a conduit of a MW resonator in the magnetic field of the MRT device. A microwave with a frequency of at least 40 GHz couples into the MW resonator for polarizing the liquid contrast agent upon passage through the conduit in the MW resonator using DNP. The contrast agent is polarized in a continuous passage in the MW resonator and administered immediately. A MW mode is formed in the MW resonator which has an antinode (Continued)

in the magnetic field strength and a node in the electric field strength. The power of the introduced microwave and coupling of the microwave into the resonator are adjusted such that in the area of the line, an amplitude of the MW magnetic field strength $$B_1 \geq 1.5 \cdot 10^{-2} Ts \frac{1}{T_{1,e}}$$

results, wherein $T_{1,e}$ is the relaxation time of the DNP-active electrons.

22 Claims, 9 Drawing Sheets

(51) Int. Cl.
*G01R 33/28* (2006.01)
*G01R 33/62* (2006.01)
*G01N 24/12* (2006.01)
*G01R 33/56* (2006.01)

(56) References Cited

U.S. PATENT DOCUMENTS 7,205,764 B1 4/2007 Anderson et al.
7,919,963 B2 4/2011 Krahn et al.
2008/0104966 A1* 5/2008 Stautner .................... 62/6

OTHER PUBLICATIONS

Weis et al. ("High-Field DNP and ENDOR with a Novel Multiple-Frequency Resonance Structure"; Journal of Magnetic Resonance 140, 293-299; 1999).*
Denysenkov, et al, "Liquid state DNP using a 260 GHz high power gyrotron", *Physical Chemistry Chemical Physics, Royal Society of Chemistry UK*, Bd. 12, Nr. 22, Jun. 14, 2010 (Jun. 14, 2010), pp. 5786-5790, XP002659804, ISSN: 1463-9076.
Stevenson, et al, "$^{13}$C Dynamic Nuclear polarization: an Alternative Detector for Recycled-Flow NMR Experiments", *Analytical Chemistry, American Chemical Society*, US, vol. 70, No. 13, Jul. 1, 1998, pp. 2623-2628, XP000776696, ISSN: 003-2700.
Vahala, et al, "A Study of the Use of Overhauser Enhancement to Assist with Needle and Catheter Placement during Interventional MRI", *Journal of Magnetic Resonance 157*, pp. 298-303, Aug. 1, 2002, XP004408078; ISSN: 1090-7807.
Wolber, et al, "Generating highly polarized nuclear spins in solution using dynamic nuclear polarization", *Nuclear Instruments & Methods in Physics Research*, Section-A: Accelerators, Spectrometers, Detectors and Associated Equipment; Jun. 21, 2004, pp. 173-181, XP004830097, ISSN: 0168-9002.
European Patent Office, International Search Report, PCT/EP2011/003125, date of mailing Sep. 23, 2011, 3 pages.

* cited by examiner

HYPERPOLARIZATION APPARATUS AND METHOD FOR ADMINISTRATION OF A HYPERPOLARIZED LIQUID CONTRAST AGENT

This application is a continuation of Patent Cooperation Treaty Patent Application PCT/EP2011/003125, filed Jun. 24, 2011, which in turn claims priority from German Patent Application 10 2010 017 568.4, filed Jun. 24, 2010, which are incorporated herein by reference.

FIELD OF THE INVENTION

The present invention lies in the field of magnet resonance tomography (MRT). In particular, it relates to an apparatus for hyperpolarization of a liquid NMR contrast agent and a method for administration of a hyperpolarized liquid contrast agent.

BACKGROUND

Magnet resonance tomography (MRT) is an imaging method, which is above all used in medical diagnostics for representing structures and functions of tissue and organs in the body. MRT is based on the principles of nuclear magnetic resonance NMR spectroscopy. For this method, the tissue to be examined is located in a strong static magnetic field, in which the spins of atomic nuclei in the examined tissue are aligned, which results in magnetization. Through resonant excitation with an electromagnetic alternating field in the radio frequency range, the magnetization can be deflected from the direction of the static field. Due to the excitation, the spins start to precess around the direction of the static magnetic field, and the precession of the overall magnetization can be measured as a voltage signal using a coil.

When the high-frequency alternating field is switched off, the spins relax back into their initial state. For this relaxation, they require a characteristic decay time, which is typical for various elements and various compounds and can be detected. Then, from this decay information, a tomographic image can be constructed.

Magnetization of the nuclear spins in the external magnetic field is a statistical process, which follows the Boltzmann distribution. Since the energy of the interaction between the nuclear spins and the static magnetic field as compared to the thermal energy at room temperature is relatively small, the overall magnetization by the static magnetic field is likewise relatively small, at the expense of the NMR signal.

One method to increase sensitivity of the NMR consists in increasing the strength of the static magnetic field, whereby a less uniform occupation of the nuclear spin states is achieved. However, there are technical limits to the strength of the magnetic field; typically, in state-of-the-art MRT devices, it is 1.5 T. With magnetic field strengths of more than 3.0 T, the patients can be moved into the magnet very slowly only, in order to minimize induced eddy currents, for example in the brain of the patient.

A further measure for increasing sensitivity consists in polarizing the sample more than what would correspond to the thermal occupation of the spin states in the given magnetic field. A sample, for which the occupancy of one or more spin states predominates compared to the other spin states clearly more than their energy difference according to the Boltzmann statistics would predict, is called hyperpolarized.

In MRT, it is known to administer a hyperpolarized fluid to a living being to be examined, i.e. a patient or an animal to be examined, which fluid generates NMR signals enhanced by several orders of magnitude. On the basis of the terminology from X-ray diagnostics, such hyperpolarized fluid is also designated as "contrast agent". Predominantly, gases are used as contrast agent. However, it is also known to inject hyperpolarized liquids into the living being to be examined.

A known technology to hyperpolarize the contrast agent represents the so-called dynamic nuclear polarization (DNP). For DNP, first, electron spins in an external magnetic field are polarized. With resonant excitations of the electron spins in the microwave range, the electron spin polarization can be transferred to the nuclear spins by means of a weak interaction between the electrons and the nuclei. The underlying mechanisms are known as Overhauser effect, solid effect, cross effect, and so-called "thermal mixing".

Herein, it is common that the contrast agent is polarized in its frozen state and in a relatively strong static magnetic field of, for example, 3.35 T. Under these conditions, the nuclear spins can be polarized considerably stronger than in the liquid state. However, in order to be able to administer the hyperpolarized contrast agent, first, it must be melted and transported to the patient. Then, the problem occurs that a substantial part of the hyperpolarization is lost due to relaxation processes upon transport. Furthermore, the method known from the state of the art is relatively complex.

SUMMARY OF THE INVENTION

The invention is based on the object of solving the problem of polarization losses described above. This object is solved by a method according to claim 1 and an apparatus for hyperpolarization of a liquid NMR contrast agent according to claim 4. Advantageous further developments are stated in the dependent claims.

For the method according to the invention, a liquid contrast agent is transported through a conduit extending along a longitudinal axis of a microwave resonator (MW resonator) arranged in the static magnetic field of the same MRT device, in which the living being to be examined is located, too. A microwave of at least 40 GHz is coupled into the MW resonator, which microwave is suited to polarize the liquid contrast agent upon passing through the conduit in the MW resonator using DNP. Strictly speaking, the liquid only becomes a "contrast agent" by means of this polarization, but for the sake of simplicity, this linguistic differentiation will no longer be made in the following. Furthermore, the contrast agent is at least at times polarized during a continuous passage through the MW resonator and immediately administered to the object to be examined in the MRT. Herein, a MW mode is formed in the MW resonator, which along at least the predominant part of the longitudinal axis of the resonator has an antinode in the magnetic field strength and a node in the electric field strength. Further, the power of the introduced microwave and coupling of the microwave into the resonator are adjusted such that in the area of at least one portion of the conduit, an amplitude of the MW magnetic field strength $$B_1 \geq 1.5 \cdot 10^{-2} Ts \frac{1}{T_{1,e}}$$

results, wherein $T_{1,e}$ is the relaxation time of the DNP-active electrons. In practice, the amplitude of the magnetic field strength $B_1$ preferably has a value of at least $1 \cdot 10^{-5}$ T, preferably at least $3 \cdot 10^{-5}$ T.

Thus, according to the invention, the MW resonator employed for polarization using DNP is arranged in the same bore of the MRT device, in which the object to be examined is located, and the contrast agent is exposed to the same static magnetic field used for MRT imaging. The contrast agent is polarized upon passage through the conduit in the MW resonator by DNP and immediately administered to the living being. Thereby, the transport of the hyperpolarized contrast agent between the apparatus for polarization and the MRT device is completely eliminated. The polarization losses inevitably associated with the transport common in the state of the art, which are particularly serious, when, the hyperpolarized contrast agent must for this purpose leave the high magnetic field used for hyperpolarization, can be drastically minimized within the scope of the invention, because the hyperpolarized contrast agent can be administered immediately following discharge from the MW resonator. Furthermore, no separate magnet is required for hyperpolarization, and no temporal coordination between hyperpolarization in one device and subsequent use of the hyperpolarized contrast agent in another device is required anymore.

The invention distinguishes itself conceptually from the common state of the art, in that the possibility of providing optimal field and temperature conditions for hyperpolarization is deliberately abandoned. The invention is based on the assumption, that the disadvantages from the less advantageous conditions for hyperpolarization can be eventually compensated by the fact that the losses between hyperpolarization and administration can be kept at a minimum, since the contrast agent is administered immediately following discharge from the resonator and while still in the same static field.

However, it is surprising for the person skilled in the art that the method can be implemented in practice at all, because the Overhauser effect, which is the predominant mechanism for DNP of liquids, decreases, as is generally known, with the external magnetic field strength. Since, however, for hyperpolarization, the magnetic field of the MRT device is used, this magnetic field strength is specified, and for state-of-the-art MRTs it normally is at least 1.5 T. Experts generally assumed that with such strong static magnetic fields, DNP in liquid is very inefficient already and in particular could not be sufficient for the purposes of the invention (also see Hausser, K. H., Stehlik, D., *Dynamic Nuclear Polarization in Liquids, Advances in Magnetic Resonance* (1968)). US 2009/0121712 A1, too, assumes, that for the use of DNP of liquids with a magnetic field of 1.5 T instead of the field of 0.35 T used therein, a reduction in efficiency by a factor of 4 to 5 has to be expected.

Furthermore, polarization of electron spins in the course of DNP requires microwave excitation with a frequency of 40 GHz or more. A microwave resonator for such high frequencies, which would be suited for the passage of a liquid, is unknown to the inventors, and it is by no means obvious that such a resonator could be manufactured at all with sufficient Q-factor despite liquid transport in the cavity. A further problem poses the residence time of the liquid in the resonator. With the residence time being too long, there is the risk that the liquid contrast agent heats up excessively; with the residence time being too short, it must be expected that the polarization achievable using DNP in the relatively strong magnetic field is not sufficient for the purposes as a contrast agent.

The inventors, however, have noticed that despite this, at the first glance, unfavorable prerequisites, it is actually possible to hyperpolarize a liquid contrast agent even in a static magnetic field of 1.5 T during passage using DNP. According to the invention, the conduit is arranged along a longitudinal axis of the resonator. Thereby, the path length in the resonator can be increased, and the residence time at a given flow rate required for a certain application is respectively prolonged. Simultaneously, the geometry of the resonator, the means for coupling the microwave into the MW resonator, the cross-section of the conduit, the power and the frequency of the microwave are adjusted with respect to one another such that a MW mode is formed in the MW resonator which along at least a predominant part of the longitudinal axis of the resonator has an antinode in the magnetic field strength and a node in the electric field strength. This results in the fact that the liquid contrast agent primarily flows through areas in which the electric field strength is low or even zero, whereby excessive heating of the liquid contrast agents can be avoided. Furthermore, the aforementioned components are tuned to one another such that in the area of at least a portion of the conduit a MW magnetic field strength $$B_1 \geq 1.5 \cdot 10^{-2} Ts \frac{1}{T_{1,e}}$$

is obtained. In practice, the amplitude of the magnetic field strength should have a value of at least $1 \cdot 10^{-5}$ T, preferably at least $3 \cdot 10^{-5}$ T. The inventors were able to verify that under these conditions, contrary to expectation, it is possible to polarize the contrast agent in passage to a sufficient extent for the purposes of MRT.

From US 2009/0121712 A1, an apparatus and a method for hyperpolarization of a liquid are known, in which the liquid is hyperpolarized using DNP in the same static magnetic field which is also used for NMR. The embodiment shown is a portable NMR device with a static magnetic field of only 0.35 T and a microwave excitation in the X-band, i.e. in a frequency range far below that of the invention. Setup and function of the microwave resonator are not described. The motivation for polarization during passage in this state of the art also does not lie in avoidance of a polarization loss between hyperpolarization and application. This state of the art rather is about visualizing the dynamics of the fluid to thereby investigate the local dynamics of water at surfaces and in the interior of hydrated materials like proteins, membranes or polymers. Therefore, in order to obtain a visible dynamic flow, a flow rate of the hyperpolarized water of 1.5 ml/min is used. In the description, investigations are described on the basis of artificial models in order to demonstrate the functional principle. The actual intended application, however, lies in the investigation of living cells, in particular of lipid double-layer membranes and other soft biological samples. Administration to a human being or to an animal for medical or diagnostic purposes using MRT, however, is not contemplated.

For DNP, it is necessary that paramagnetic substances are present in the contrast agent, which in the following are also called paramagnetic centers. In a preferred embodiment, the paramagnetic centers are dissolved in the contrast agent. In addition or alternatively, the paramagnetic centers, however, can also be immobilized, for example fixedly bound to a gel, for example an agarose or silica gel. As paramagnetic centers may serve, for example, stable radicals, in particular TEMPOL and its derivatives, trityl, potassium nitrosodisulfonate, paramagnetic transition metal ions, radicals generated by ionized radiation, and molecules in their triplet state.

Preferably, the apparatus for hyperpolarization and administration of a liquid NMR contrast agent comprises a first conduit suitable for transporting the contrast agent from a reservoir outside a bore of the MRT to the resonator, when this is arranged in the bore of the MRT, and/or a second conduit suitable for transporting the hyperpolarized contrast agent from the resonator to the living being to be examined, when this is likewise located in the bore of the MRT.

Herein, the cross-section of the second conduit is preferably smaller than that of the conduit in the MW resonator. As a consequence, the flow velocity in the second conduit, i.e. between the MW resonator and the patient, is higher than in the resonator. Thereby, for the predetermined required dose of contrast agent per time, a longer residence time in the resonator is compatible with a shortened transport between the resonator and the living being.

Preferably, the MW resonator has portions, which for setting of the resonance frequency can be adjusted relative to one another, and means for adjusting the resonator portions relative to one another, which preferably are accessible from outside the bore of the MRT, when the MW resonator is arranged therein. Thereby, the MW resonator can be easily tuned to the MW frequency that achieves the best DNP result. It must be noted that the spin excitation frequency depends on the paramagnetic substance used. Such a tunable MW resonator is therefore even suitable for commercial applications in the hospital environment, where in routine operation no modifications are undertaken at the apparatus, because the MW resonator then becomes usable in a more diversified fashion.

In a possible embodiment, the MW resonator is designed such that the irradiated MW frequency corresponds to a fundamental oscillation of the resonator. In an advantageous further development, however, the dimensions of the MW resonator are tuned to a frequency of the MW source such that this frequency corresponds to a MW mode in the resonator which in respect of the longitudinal axis of the resonator represents a harmonic. This means that—for a predetermined MW frequency—the dimension of the MW resonator along the longitudinal axis can be a multiple of the length, which would result for an operation in the fundamental oscillation. This enables an increased length of the resonator along the longitudinal axis, whereby the distance covered by the contrast agent within the resonator can be increased as well, which again enables a respective increase of the residence time in the MW resonator, for a given dose rate and a predetermined cross-section of the conduit in the resonator. Furthermore, the inventors noticed that hereby the quality of the MW resonator can be increased, too. It is to be noted that in the very short-wave microwave range present here, it is not readily possible to choose the cross-section of the conduit randomly, because with the cross-section being too large, the Q-factor of the MW resonator is reduced. Thus, for a certain desired dose rate for the application of the NMR contrast agent, it is not possible to achieve randomly high residence times of the contrast agent in the resonator by respectively enlarging the cross-section of the conduit in the resonator. For this reason, it is advantageous to increase the length of the resonator along the longitudinal axis in the manner stated.

Preferably, the MW resonator is electrically conductive at its surface facing the MW field. In particular, the MW resonator can at least partially consist of a carrier material, which on its surface facing the MW field is coated with a well conducting layer, in particular a silver layer. Note that for the microwave frequencies in the high GHz range present here, considerable requirements are made to the precision of the resonator, which are not comparable to the far lower requirements, for example, for X-band resonators. With the suggested setup with a coated carrier material, it is possible to use a carrier material that can be processed sufficiently well, without being restricted in the selection to particularly well conductive materials. The thickness of the conductive layer should be a few skin depths. Preferably, its thickness is at least 0.5 µm, particularly preferred 1 µm, and in particular at least 2 µm.

Preferred carrier materials are formed by bronze, brass or red brass alloys, aluminum, copper or nickel silver. The alloys stated are preferably annealed in order to guarantee the required geometrical precision. A particularly advantageous embodiment uses a hydrogen-free plastic as carrier material, which has the advantage that it does not generate a NMR background signal. Preferred plastics in this regard are PCTFE, Vespel or PTFE.

As mentioned above, there are limits to the achievable dose rate due to the restriction of the size of the resonator, the limited cross-section of the conduit and the required residence time of the contrast agent in the resonator. Therefore, in an advantageous further development, a multitude of resonators of the type above mentioned are used, through which the contrast agent flows in parallel. In this manner, the individual resonators can be optimized in respect of their function independent of the flow rate, and a desired flow rate can be achieved by a respective number of resonators.

Preferably, an apparatus for tempering, in particular heating the contrast agent, is provided, which is arranged upstream of the MW resonator, when viewed in the flow direction of the contrast agent. In addition or alternatively, an apparatus for tempering, in particular heating the contrast agent, can also be arranged directly downstream of the MW resonator. With these apparatuses, it can be ensured that the temperature of the contrast agent is optimally adjusted for polarization in front of the resonator and for the transfer behind the resonator, since with an increased temperature, the relaxation time $T_1$ is increased. In addition to that, prior to injection into the object to be examined, the temperature can be regulated to a value adjusted to the object to be examined, in particular to the body temperature of a living subject.

In a particularly advantageous embodiment, the resonator is a cylinder resonator. Its geometry is preferably tuned to the frequency of the MW source, such that the frequency corresponds to a $TE_{011}$ or a $TE_{012}$ mode in the resonator.

Preferably, the MW resonator has a cylindrical resonator portion, which at least one longitudinal end is terminated by a piston or prop adjustable along the longitudinal axis of the resonator. Thereby, the resonator can be easily tuned to a desired resonance frequency.

For the present high MW frequencies of more than 40 GHz, however, the resonator must be tuned with highest precision. In an advantageous further development, the at least one adjustable piston or prop therefore has an outer thread, which is engaged with an inner thread provided at the resonator, such that the piston or prop is adjustable in the direction in parallel to the longitudinal axis of the MW resonator by rotation around its axis. In an advantageous further development, the piston can be rotated by a worm gear for adjustment.

Preferably, the cylinder resonator has an inner diameter of 8.4-15 mm, particularly preferred 8.7-11 mm, and particularly preferred of 9.0-9.4 mm. If the diameter is chosen too large, a multitude of undesired modes can result in the resonator.

In an advantageous further development, the cylinder resonator is adjustable in its length between 11.0 and 12.0 mm (for the $TE_{011}$ mode) or between 22.0 and 24.0 mm (for the $TE_{012}$ mode). With this adjustability, the matching resonance frequencies for different radicals can be set. If even higher modes are to be excited, the length range stated above can be respectively multiplied.

Preferably, an iris is provided for coupling the electrical field component of the microwave into the MW resonator. The selection of the iris has a decisive influence on the so-called conversion factor of the resonator. Preferably, the iris is a slit iris, which preferably has a slit width of 0.01-1 mm, particularly preferred of 0.2-0.4 mm, and/or a length of 1-10 mm, preferably 5-7 mm. In an advantageous further development, the iris can be adjusted in size. This has the advantage that in operation, it can be optimally adjusted to the resonator and the conduit, which for the high microwave frequencies present here likewise is substantially more delicate than, for example, for microwaves in the X-band.

Alternatively, however, it is also possible to provide means for coupling the magnetic field component of the microwave into the resonator.

BRIEF DESCRIPTION OF THE DRAWINGS

Further advantages and characteristics of the invention become apparent from the following description, in which the method for administering a hyperpolarized liquid contrast agent and an associated apparatus are explained on the basis of a preferred embodiment referring to the enclosed drawings. Therein.

DETAILED DESCRIPTION OF THE INVENTION

Figure 1:
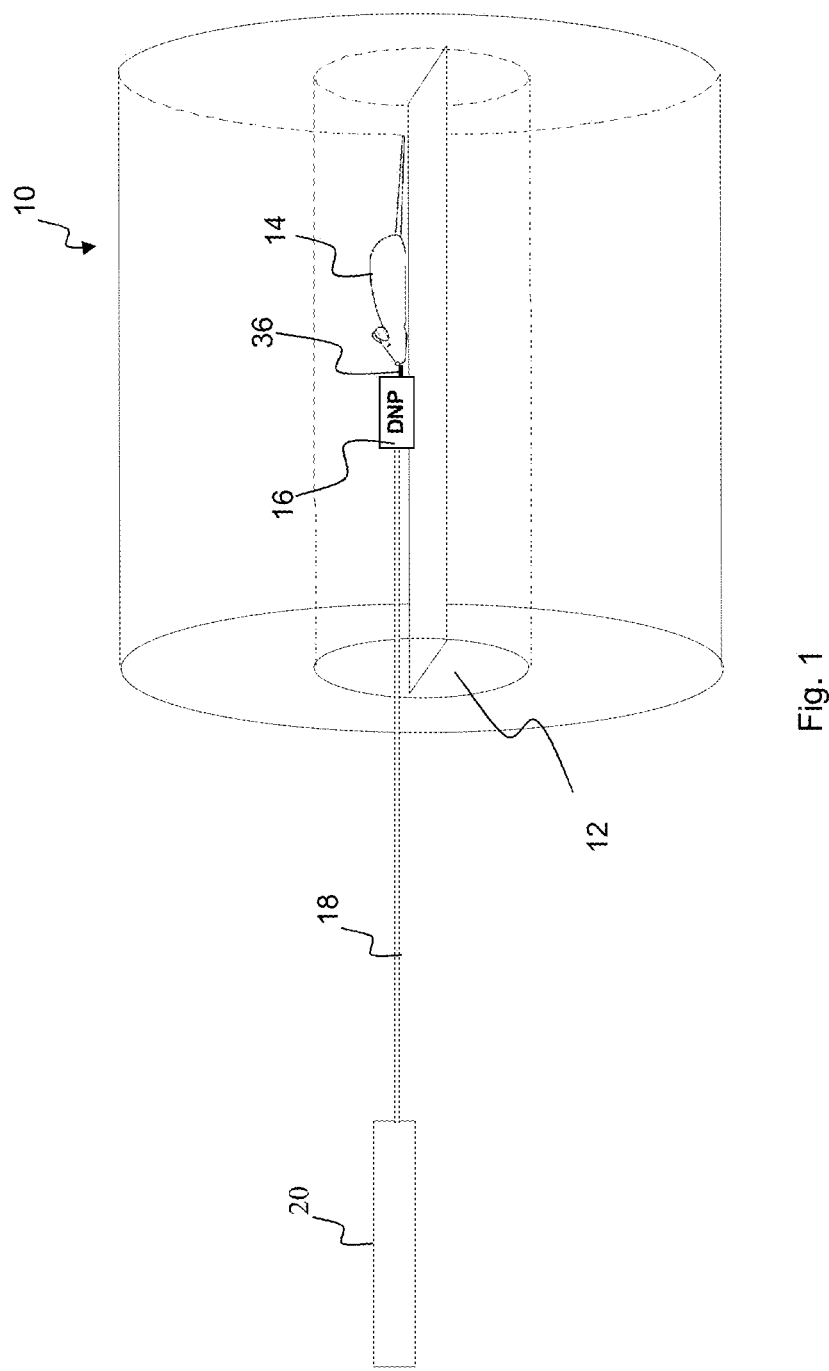
FIG. 1 is a schematic representation of a MRT device, in the bore of which an animal to be examined and an apparatus for polarization of a liquid NMR contrast agent are located.

In FIG. 1, a magnet 10 of a MRT device is represented schematically. The magnet 10 has a bore 12 in which a static magnetic field with a strength of 1.49552 T is generated. Furthermore, in the MRT device, as customary, means for generating a high-frequency field for the resonant excitation of nuclear spins as well as means for generating a magnetic gradient field for imaging are provided, which, however, are not shown in the figure.

As further shown in FIG. 1, a living being to be examined 14, a mouse in the example shown, is located in the bore 12 of the magnet 10. The apparatus and the method of the invention, however, are likewise and particularly usable for applications in human medicine.

Furthermore, a MW resonator 16, which is connected with a microwave source 20 via a waveguide 18, is located in the bore 12 of the magnet 10. In the embodiment shown, the microwave source 20 is suitable for generating microwaves with frequencies in a range from 41 GHz to 43 GHz. The MW resonator 16 is intended to polarize a NMR contrast agent flowing therethrough using DNP. The supply conduit of the contrast agent is not shown in FIG. 1.

Figure 2:
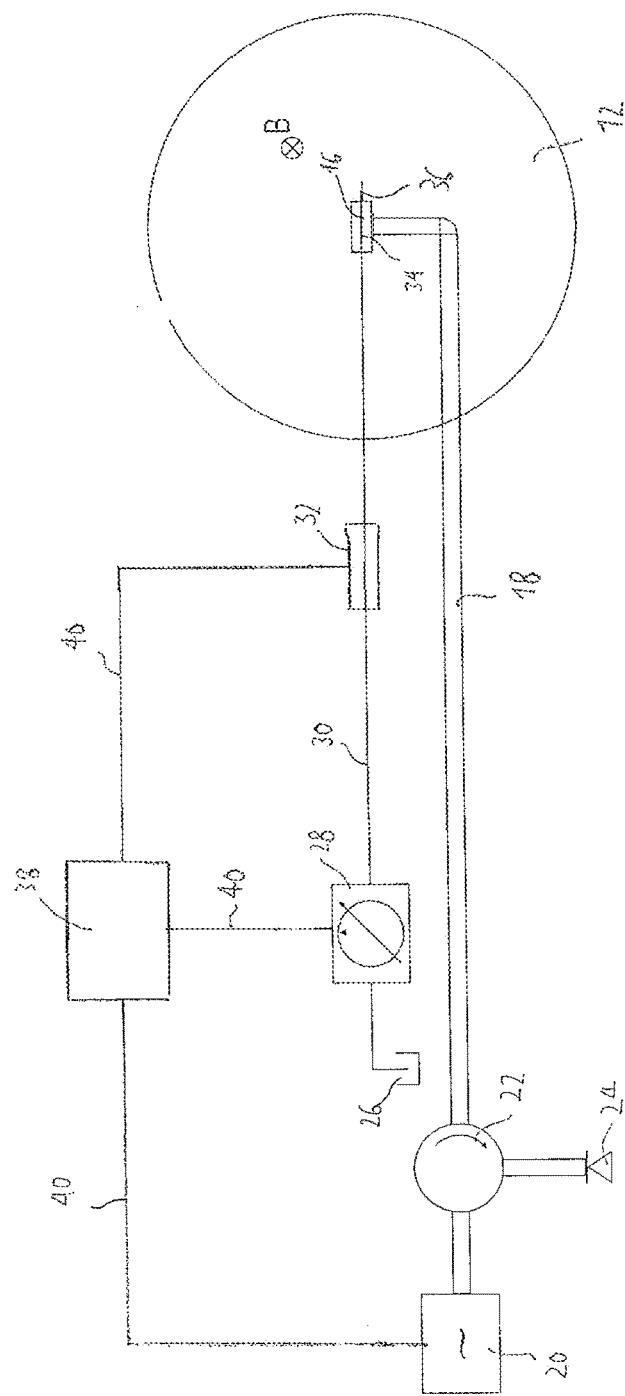
FIG. 2 is a block diagram of substantial components of the apparatus of FIG. 1, FIG. 3 are three sectional views of a cylinder resonator for use in the apparatus of FIGS. 1 and 2.

FIG. 2 shows a block diagram of further components of the apparatus for hyperpolarization of the liquid NMR contrast agent. In FIG. 2, as in FIG. 1, the bore 12 of the magnet 10, the microwave source 20 and the waveguide 18 are represented schematically. Furthermore, a MW circulator 22 and a receiver diode 24 are represented, which serve for finding the resonance conduits and setting the resonance frequency of the resonator.

Furthermore, a reservoir 26 for a hyperpolarizable liquid is shown in FIG. 2, which in the present description for the sake of simplicity is called "NMR contrast agent"—in analogy with the terminology from X-ray diagnostics. The function of the hyperpolarized contrast agent is to amplify the NMR signals by its degree of polarization, which lies far above the degree of polarization according to the Boltzmann distribution under the given conditions. It is understood that, strictly speaking, the liquid only becomes a contrast agent following hyperpolarization, however, for the sake of simplicity, the unpolarized as well as the hyperpolarized liquid is called NMR contrast agent in the present description.

Furthermore, a pump 28 is shown in FIG. 2, which is suitable for continuously transporting the NMR contrast agent from the reservoir 26 through a first conduit 30 to the MW resonator 16 in the bore 12. In the flow path of the NMR contrast agent along the first conduit 30, an apparatus 32 for temperating the same is provided. Using such apparatus 32, the liquid contrast agent, for example, can be cooled to a degree that following the unavoidable heating in the MW resonator 16, it is close to the body temperature of the living being 14. Although not shown in FIG. 2, a further apparatus for temperating may also be provided between the resonator 16 and the living being 14.

In the MW resonator 16, the contrast agent then flows through a conduit 34, which is described in detail below. Downstream of the MW resonator 16, there is a second conduit 36, which leads to the living being 14 (in FIG. 2 not shown in its entirety). In the preferred embodiment, the cross-section of the second conduit 36 is smaller than that of conduit 34 in the MW resonator 16, so that with the same flow rate, the flow velocity is increased, i.e. the flow time between the MW resonator 34 and the living being 14 is reduced in order to keep the losses in polarization as low as possible.

Finally, a control device 38 is provided in FIG. 2, which for controlling the microwave source 20, the pump 28 and the apparatus for temperating 32 is connected therewith via the control lines 40.

Next, the function of the apparatus of FIGS. 1 and 2 is explained. One particularity of the apparatus of FIGS. 1 and 2 consists in the fact that the NMR contrast agent is polarized using DNP in the same magnetic field, in which the MRT is performed, too, and that the hyperpolarization takes place, at least at times, continuously with the administration to the living being 14. Thereby, the transport of the hyperpolarized contrast agent from an apparatus for hyperpolarization to the MRT device as commonly employed in the state of the art can be omitted. This, on the one hand, has advantages in respect of handling and procedural economy. A further important advantage is that the contrast agent is administered immediately following its hyperpolarization, so that between hyperpolarization and administration comparatively small polarization losses occur. These polarization losses are a substantial problem in the state of the art where the contrast agent must be transported between hyperpolarization and administration and often still needs to be melted.

Hyperpolarization takes place in the MW resonator 16 while the contrast agent is passed therethrough in conduit 34. The contrast agent has atomic nuclei with nuclear spins, which can be aligned in the magnetic field. In the simplest case, this can be the hydrogen nuclei of water, but other nuclei, e.g. $^{13}C$, can be used, too. Further important contrast agents are, for example, pyruvate and lactate, which can be used as metabolism marker. Furthermore, for hyperpolarization using DNP, paramagnetic centers or unpaired electrons must be present. These can be formed by stable radicals, as for example 4-hydroxy-2,2,6,6-tetramethylpiperidin-1-oxyl (TEMPOL) or TEMPOL derivatives, Fremy's salt or the like, by paramagnetic transition metal ions in solution or in solids. Further examples for paramagnetic centers are molecules in their triplet state or radicals in crystals generated by ionization. The radicals can be solved in the contrast agent itself and/or bound to a molecule, in particular a target molecule. Alternatively, the paramagnetic centers, however, can also be immobilized, for example bound to a gel, which is arranged in conduit 34 in the MW resonator 16. It is also possible to separate the radicals or their carriers, respectively, from the solution prior to administration.

Depending on the application and the NMR contrast agent used, different residence times of the contrast agent in the MW resonator 16 can be advantageous. Preferred residence times are between a few seconds and 100 milliseconds. The flow velocity is preferably chosen such that at the imaging target, a maximum polarization is achieved. This depends on the geometry of the flow system and the speed of the polarization setup, which for its part depends on the radicals used or their concentration. The polarization achieved is, to a certain degree, also power-dependent. The correct choice of the flow velocity also depends on the relaxation speed of the hyperpolarized nuclei. Preferred flow velocities lie between 1 mm/s to 1 m/s, which for the conduit used in the embodiment corresponds to a flow of 1.8 ml/h to 1800 ml/h. Preferred flow rates are 6 to 12 ml/h.

It is advantageous when flow velocity and residence time can be optimized in respect of the polarization result and are not additionally restricted in respect of a desired dose rate for administration. This in particular applies in cases where higher dose rates are required, which cannot be simply achieved with larger cross-sections of conduit 34, because a larger conduit diameter deteriorates the Q-factor of the microwave resonator 16. Instead, it can be advantageous to operate several resonators with lower cross-section conduits in parallel (not shown).

Figure 3:
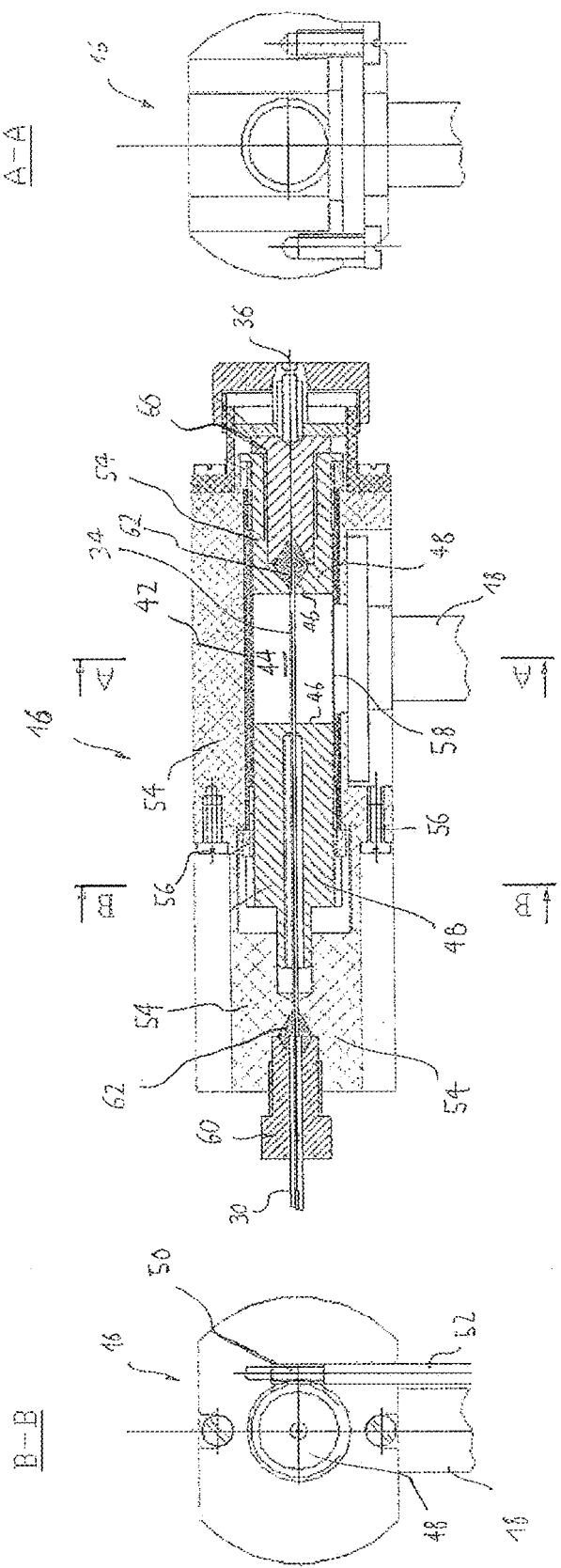

FIG. 3 shows an example for the MW resonator 16, which is a cylinder resonator.

The cylinder resonator comprises a red brass cylinder 42, which on its inner side is coated with a silver layer in order to increase the conductivity at the resonator inner wall. The conductive layer should have a thickness of a few skin depths of the microwaves. In the present example, the skin depth of the microwaves is a few 100 nm, and the silver layer has a thickness of 2 µm. In the interior of the red brass cylinder 42, a cylindrical resonator cavity 44 is formed.

The resonator cavity 44 is limited or terminated by front faces 46 of brass pistons 48 at the end surfaces of the cylinder, which at their front faces 46 are likewise coated with silver. The left-hand brass piston 48 can be adjusted along the longitudinal axis of the cylinder cavity 44. For that, an outer thread is formed at its external surface which is engaged with an inner thread in the red brass cylinder 42. Thus, by rotating the piston 48, the axial length of the cylindrical resonator cavity 44 can be set precisely. As shown in the sectional view B-B, the piston 48 can be rotated for its adjustment via a screw 50, which is engaged with a thread (not shown) at the outer circumference of the piston 48 and drives the same in the manner of a worm drive. The screw 50 has an elongated shaft 52 via which it can be used from outside the bore 12 of the MRT magnet. Thereby, the MW resonator 16 in the bore 12 can be tuned.

The MW resonator 16 has a multi-part fixture made of a hydrogen-free plastic, in the embodiment shown made of Vespel. The individual portions 54 of the fixture are tightened with screws 56.

As can be further noted in FIG. 3, the microwave is coupled into the resonator cavity 44 via the waveguide 18 and a slit iris 58. In the embodiment shown, the slit iris 58 has a length of 5.5 mm and is therefore slightly shorter than the diameter of the waveguide, which is 5.6 mm. The width of the iris is between 0.01 and 1 mm, in the specific embodiment 0.29 mm. The inventors have noticed that for the design of the iris in respect of efficient coupling in, a precision is required which is substantially higher than that required for longer wavelengths, for example in the X-band. It has proven advantageous to manufacture the iris 58 with the erosion method in order to guarantee the required precision.

Finally conduit 34 is seen in FIG. 3, which is connected with the first or second conduit 30, 36, respectively, in the sealing piston 60. For sealing the transitions between the portions of the conduit, a Teflon seal 62 is provided, which is compressed when the sealing pistons 60 are tightened to the fixture 54 (on the left in FIG. 3) or the piston 48 (on the right in FIG. 3), respectively.

Figure 4:
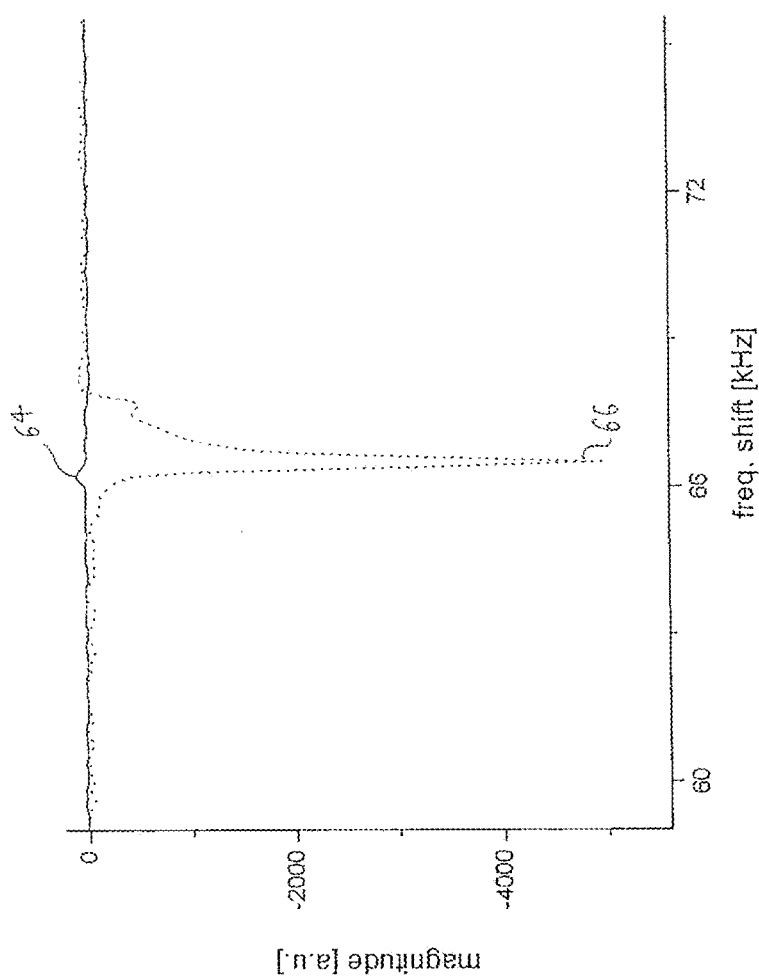
FIG. 4 shows NMR spectra recorded with stationary contrast agent in the resonator of FIG. 3 with and without microwave irradiation.
Figure 5:
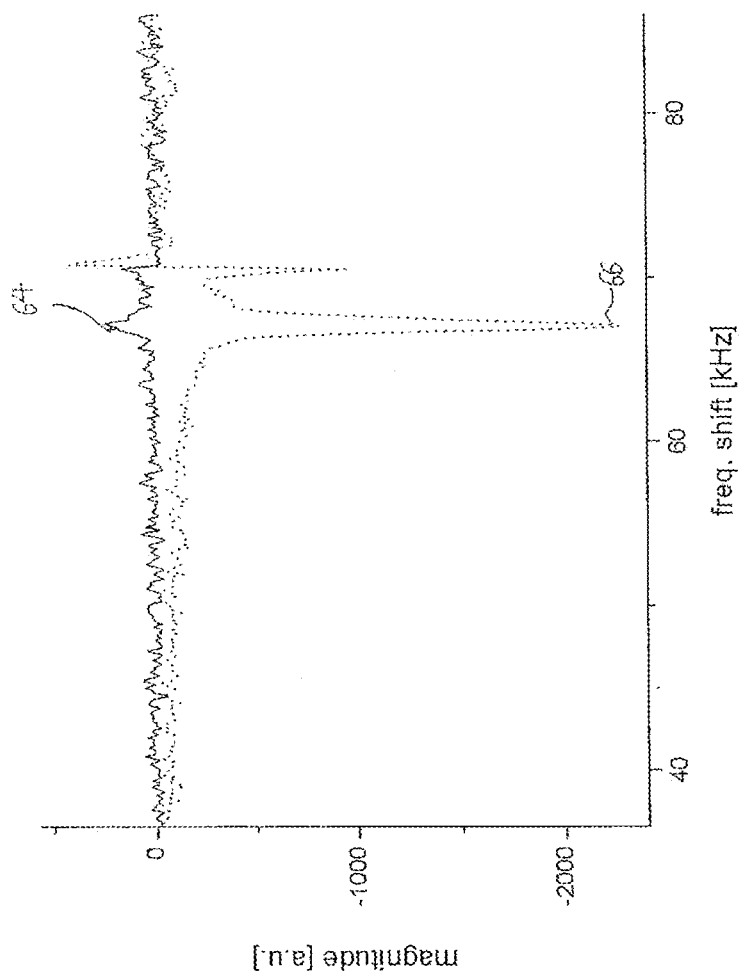
FIG. 5 shows NMR spectra recorded with flowing contrast agent with and without MW irradiation.

FIGS. 4 and 5 show NMR spectra of a proton signal in water with a frequency shift of approx. 66 kHz, which were generated using the resonator 16 of FIG. 3. The continuous line respectively shows the comparative case, wherein no microwave was radiated into the resonator 16, and the broken line respectively shows the case with a MW irradiation of 2 W. FIG. 4 shows the NMR signals for the case where the contrast agent is stationary in conduit 34 in the resonator 16, and FIG. 5 shows the case where the contrast agent flows through the resonator 16 with a flow rate of 8 ml/h. Here, water with 12 mmol/l of TEMPOL was used as the contrast agent.

In FIG. 4, it can be seen that with a stationary contrast agent, the normal NMR signal 64 can be enhanced by a factor of −98 as a consequence of hyperpolarization using DNP (comp. signal 66). This is an extraordinary and surprising result, which was not predictable for a liquid contrast agent with such high magnetic field strengths and a respectively high microwave frequency. From FIG. 5, it can be seen that even during flow of the contrast agent, an enhancement factor of −14 results as a consequence of hyperpolarization. This indicates that the method according to the invention and the apparatus for hyperpolarization according to the invention are in fact very much suited for increasing the NMR sensitivity, and in particular in MRT promise considerable improvements compared to the state of the art.

Figure 6:
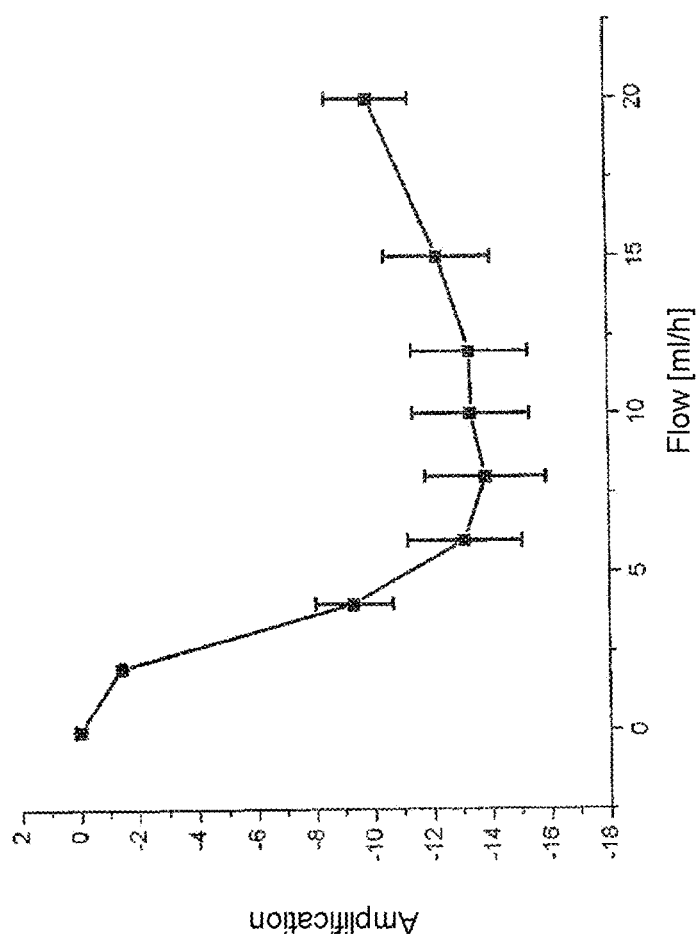
FIG. 6 shows the amplification of the NMR signal depending on the flow rate of the contrast agent.

With regard to the strength of the hyperpolarization of the contrast agent in the object to be examined is, the flow velocity of the contrast agent through the microwave resonator is of importance. On the one hand, a lower flow rate results in a longer residence time in the resonator, and thereby in stronger hyperpolarization. On the other hand, the flow time between the MW resonator and the object to be examined is the longer, the lower the flow rate is. During the transfer between the MW resonator and the object to be examined, part of the hyperpolarized nuclear spins are relaxed into the thermal equilibrium state, whereby the hyperpolarization as a whole decreases. In practice, a compromise must therefore be found between short transfer times between MW resonator and object to be examined (i.e. high flow velocities) and sufficient residence times in the MW resonator (i.e. low flow velocities). This compromise can be determined by way of experiments. For example, FIG. 6 shows the amplification of the NMR signal depending on the flow rate. As can be seen therein, for the present geometry, the absolute value of the amplification is highest when the flow rate is between 6 and 12 ml/h. The described compromise can be partially resolved by the fact that the cross-section of the conduit, through which the contrast agent is transported between the MW resonator and the object to be examined, is smaller than the cross-section of the conduit within the MW resonator, such that during the transfer from the MW resonator to the object, the contrast agent flows faster than within the MW resonator.

Figure 7:
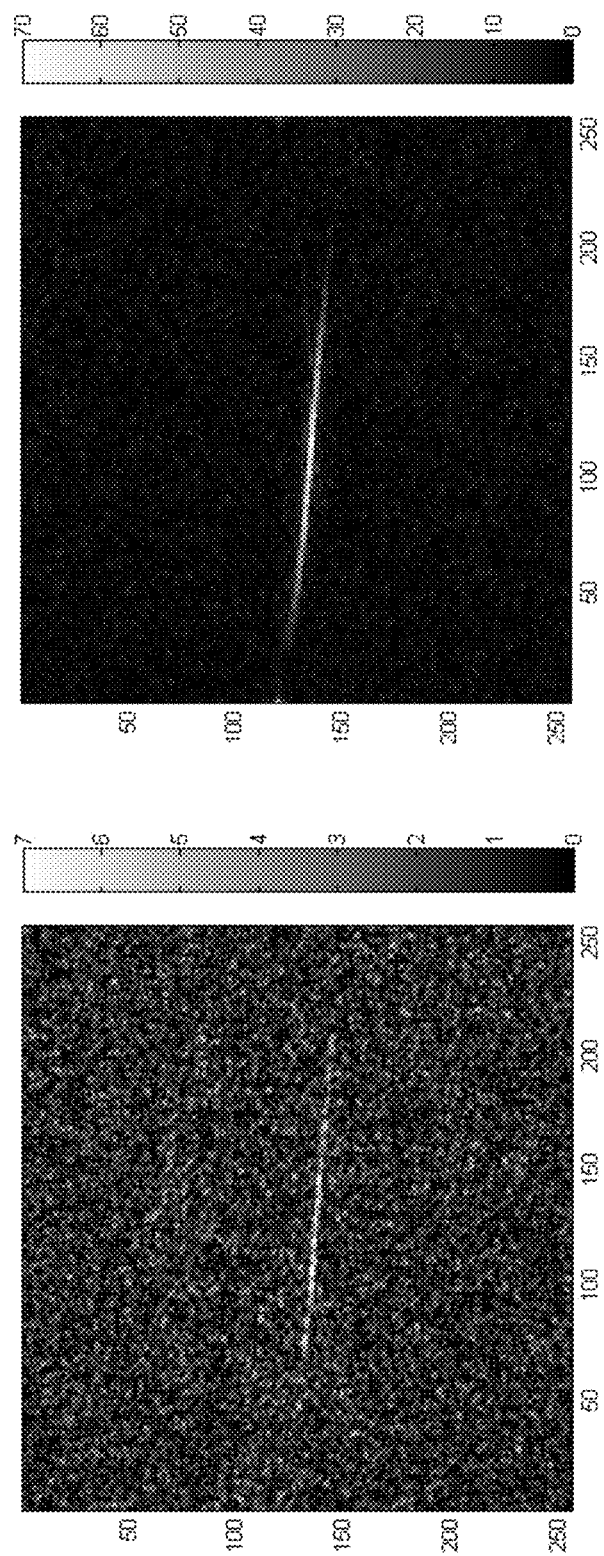
FIGS. 7A-B are MRI images of a capillary, through which contrast agent is flowing, with and without DNP.

FIG. 7 shows results of a test application of the apparatus of the invention. Therein, the contrast agent, following its discharge from the MW resonator, was transported through a glass capillary with a diameter of 0.15 mm Such a capillary is of a similar size as a small blood vessel. FIG. 7a shows the MRI image without DNP, i.e. for the case where the MW resonator is not active. In case of FIG. 7a, eight scans were required to make the interior of the capillary visible at all.

FIG. 7b shows the case where the MW resonator is switched on and the contrast agent is hyperpolarized using DNP. As can be seen from FIG. 7b, the capillary can be made visible in a single MRI scan. In both images, the sensitivity distribution of the imaging coil can be noticed, since the signal drops on the length scale of the imaging coil, which in the case shown is about 20 mm.

Figure 8:
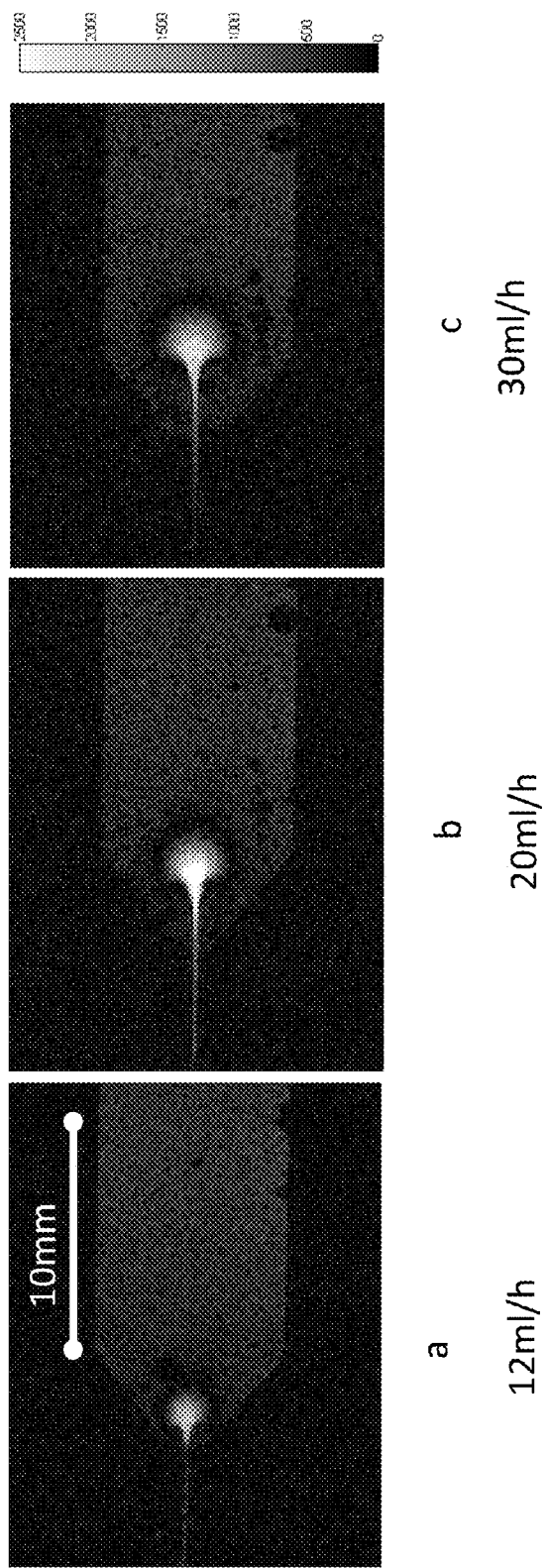
FIGS. 8, 9 are MRI images of a flat cell, through which contrast agent is flowing.

FIG. 8 shows an example measurement, in which the hyperpolarized contrast agent is transported through a flat cell, in which a sample with thermal polarization is located. FIG. 8a shows the NMR signals at a flow rate of 12 ml/h, FIG. 8b at a flow rate of 20 ml/h, and FIG. 8c at 30 ml/h. In all cases, the dispersion and the decay of the hyperpolarization are well recognizable. Since the cell has a homogenous thickness, the images of 8a-8c show no volume effects, i.e. each pixel in the two-dimensional image represents the same volume of contrast agent. Insofar, the NMR intensity shown represents the net magnetization of the respective voxel. From the comparison of FIGS. 8b and 8c, it becomes clear that a higher flow velocity results in a larger hyperpolarized jet; at the same time, however, the lower flow rate in FIG. 8b results in increased signal intensity, i.e. leads to a better polarization transfer. This again shows that depending on the application, the flow rate should be adjusted to the underlying geometry.

Upon close consideration of FIG. 8, it is noticeable that, immediately following entry into the flat cell, the NMR intensity of the hyperpolarized contrast agent jet is not as high as a little downstream thereof, when the contrast agent is slightly diffused and slowed down. The reason for that is the relatively high speed with which the hyperpolarized contrast agent moves through the gradient fields, which results in dephasing and thus in a weaker signal. This effect becomes stronger when imaging sequences are used, which are particularly sensitive to this kind of dephasing, as for example the spin echo sequence. This effect can be utilized to actively suppress the signal for the fastly moved contrast agent, while the signal for the contrast agent at lower speeds is more pronounced.

Figure 9:
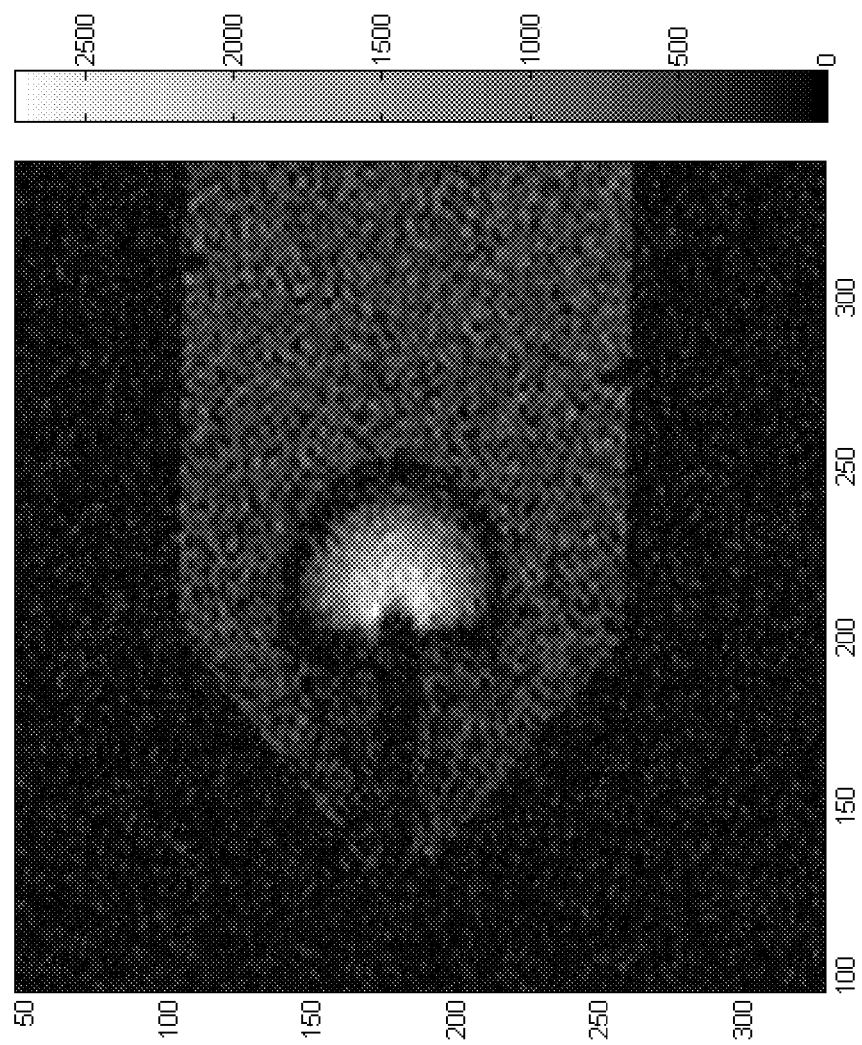

One example for that is shown in FIG. 9, wherein the intensity in the areas, where the contrast agent moves slowly, is similar to FIG. 8. The areas with high flow velocity, on the contrary, despite hyperpolarization, result in an almost vanishing signal.

In the embodiment shown, hyperpolarization was achieved by the $TE_{011}$ mode, which has a node in the electrical field strength along the longitudinal axis of the cylinder cavity 44, i.e. in the area of conduit 34, and in this area has an antinode in the magnetic field strength.

Although in the present example a cylinder resonator was used, the invention is not restricted to this. In particular, as an alternative to a closed, i.e. cavity resonator like the cylinder resonator shown, open resonators, for example Fabry-Perot resonators, are suitable, too, which due to their kind of structure favor dissipation of the heat generated in the contrast agent by the microwave field. Therefore, the teaching of the invention can also be applied to other types of resonators. What matters is that the geometry of the resonator, the means for coupling the microwaves into the MW resonator, the cross-section of the conduit, the power and the frequency of the MW source are adjusted or tuned to one another such that a MW mode can be formed in the MW resonator, which along at least a predominant part of a longitudinal axis of the resonator has an antinode in the magnetic field strength and a node in the electric field strength, and in the area of at least one portion of the conduit, a MW magnetic field of preferably at least $$1.5 \cdot 10^{-2} Ts \frac{1}{T_{1,e}}$$

can be generated, preferably a MW magnetic field of $1 \cdot 10^{-5}$ T, particularly preferred of at least $3 \cdot 10^{-5}$ T.

REFERENCE LIST

10 MRT magnet
12 Bore in MRT magnet 10
14 Living being
16 MW resonator
18 Microwave conductor
20 Microwave source
22 Circulator
24 Receiver diode
26 Reservoir for NMR contrast agent
28 Pump
30 First conduit
32 Apparatus for temperating
34 Conduit in resonator 16
36 Second conduit 38 Control equipment
40 Control line
42 Red brass cylinder
44 Cylinder cavity
46 Front face
48 Piston
50 Screw
52 Extended shaft of screw 50
54 Plastic fixture
56 Screw
58 Slit iris
60 Sealing piston
62 Teflon seal
64 NMR signal without hyperpolarization
66 NMR signal with hyperpolarization

The invention claimed is:

1. A method for providing a hyperpolarized liquid contrast agent for use in a magnetic resonance tomography (MRT) device, in particular for administration to a living being in the MRT device, comprising the following steps:
  passing said liquid contrast agent through a conduit extending along a longitudinal axis of a microwave (MW) resonator arranged in a magnetic field of said MRT device,
  coupling of a microwave of at least 40 GHz at an adjustable power into said MW resonator that is suitable for polarizing said liquid contrast agent upon its passage through said conduit in said MW resonator using dynamic nuclear polarization (DNP),
  wherein said contrast agent, at least at times, is polarized in said MW resonator during a continuous passage through the MW resonator at a flow velocity at least 1 mm/s and no more than 1 m/s, and administered immediately to said living being,
  wherein in said MW resonator, a microwave (MW) mode is formed, which along all or most of said longitudinal axis of said MW resonator has an antinode in the MW mode magnetic field strength and a node in the MW mode electric field strength,
  and wherein the adjustable power of the introduced microwave and the coupling of said microwave into said MW resonator are adjusted for the MW mode magnetic field strength to be at least $1 \cdot 10^{-5}$ T in an area of at least a portion of said conduit.

2. The method according to claim 1, wherein at least one paramagnetic substance is dissolved in said contrast agent or at least one immobilized paramagnetic substance is provided, which is arranged in the flow of said contrast agent, wherein said paramagnetic substances are in particular formed by one or more of the following substances: 4-hydroxy-2,2,6,6-tetramethylpiperidin-1-oxyl (TEMPOL) and TEMPOL derivatives, trityl, potassium nitrosodisulfonate, paramagnetic transition metal ions, radicals generated by ionized radiation, and molecules in their triplet state.

3. An apparatus for hyperpolarization of a liquid nuclear magnetic resonance (NMR) contrast agent, comprising:
  a microwave (MW) resonator having a longitudinal axis and configured for forming a microwave (MW) mode, which along all or most of said longitudinal axis has a magnetic field strength antinode and an electric field strength node,
  a conduit for said liquid NMR contrast agent, said conduit having a conduit cross-section and extending along said longitudinal axis of said MW resonator,
  a microwave source for generating microwaves at an adjustable power with a frequency of at least 41 GHz, means for coupling microwaves generated with said microwave source into said MW resonator, and
  a pump configured for continuously transporting said contrast agent through said conduit in said MW resonator at a flow velocity of at least 1 mm/s and no more than 1 m/s, and for administrating it to a living being,
  wherein said MW resonator, said means for coupling said conduit, and said microwave source are configured for generating a MW magnetic field of at least $1 \cdot 10^{-5}$ T in at least a portion of said conduit.

4. The apparatus according to claim 3, wherein said MW resonator and said MW source are configured to generate microwaves at a frequency that corresponds to the MW mode in the MW resonator, which in respect of said longitudinal axis of said MW resonator represents a harmonic.

5. The apparatus according to claim 3, further comprising a multitude of resonators, through which contrast agent flows in parallel.

6. The apparatus according to claim 3, wherein said conduit comprises one or both of:
  a first conduit suitable for transporting said contrast agent from a reservoir outside a bore of a magnetic resonance tomography (MRT) device to said MW resonator, when said MW resonator is arranged in said bore of said MRT device, and
  a second conduit suitable for transporting said hyperpolarized contrast agent from said MW resonator to said living being, when said resonator is located in the bore of the MRT device.

7. The apparatus according to claim 6, wherein the cross-section of said second conduit is smaller than that of said conduit in said MW resonator.

8. The apparatus according to claim 3, wherein said MW resonator has an adjustable resonance frequency.

9. The apparatus according to claim 8, where said resonance frequency is adjustable from outside a bore of a magnetic resonance tomography (MRT) device when said MW resonator is arranged therein.

10. The apparatus according to claim 3, wherein said MW resonator is electrically conductive at its surface facing the microwave field.

11. The apparatus according to claim 10, wherein said MW resonator includes a carrier material having a surface facing said MW field, wherein said surface is coated with a conductive layer.

12. The apparatus according to claim 11, wherein said conductive layer has a thickness of at least 0.5 μm.

13. The apparatus according to claim 11, wherein said carrier material is formed by any of the following materials: bronze, brass or red brass alloys, aluminum, copper, nickel silver, PCTFE hydrogen-free plastic, Vespel hydrogen-free plastic, and PTFE hydrogen-free plastic.

14. The apparatus according to claim 3, wherein said MW resonator is a cylinder resonator.

15. The apparatus according to claim 14, wherein said cylinder resonator has an internal diameter of 8.4 to 15 mm.

16. The apparatus according to claim 14, wherein said cylinder resonator can be adjusted in said cylinder resonator's length between 11 and 12 mm, between 22 and 24 mm, or between $11 \cdot n$ mm and $12 \cdot n$ mm, wherein n is an integer and $2 < n < 100$.

17. The apparatus according to claim 14, wherein the MW mode is a transverse electric (TE)011, a TE012 or a TE01n mode with $2 < n < 100$.

18. The apparatus according to claim 17, wherein said MW resonator has a cylindrical resonator portion, which at least at one longitudinal end is terminated by a piston or prop adjustable along said longitudinal axis of said resonator.

19. The apparatus according to claim 18, wherein said at least one adjustable piston or prop has an external thread engaged with an internal thread provided at said MW resonator, and wherein said piston or prop is adjustable in the direction in parallel to said longitudinal axis of said cylinder resonator by rotation around said cylinder resonator's axis.

20. The apparatus according to claim 14, wherein the means for coupling microwaves comprises an iris for coupling said microwaves into said MW resonator.

21. The apparatus according to claim 20, wherein said iris is a slit iris with a slit width of 0.01 to 1.00 mm.

22. The apparatus according to claim 20, wherein said iris can be adjusted in size.

* * * * *